United States Patent
Kucharski et al.

(10) Patent No.: US 11,141,045 B2
(45) Date of Patent: *Oct. 12, 2021

(54) ENDOSCOPE WITH VARIABLE PROFILE TIP

(71) Applicant: EnlightenVue LLC, Denver, CO (US)

(72) Inventors: Robert C. Kucharski, Denver, CO (US); Paul I. Bloom, New York, NY (US); Giacomo Basadonna, Haddam, CT (US); Larry O. Blankenship, Boudler, CO (US); Laura E. Bucknam, Arvada, CO (US)

(73) Assignee: EnlightenVue LLC, Denver, CO (US)

( * ) Notice: Subject to any disclaimer, the term of this patent is extended or adjusted under 35 U.S.C. 154(b) by 636 days.

This patent is subject to a terminal disclaimer.

(21) Appl. No.: 15/885,527

(22) Filed: Jan. 31, 2018

(65) Prior Publication Data

US 2018/0249888 A1 Sep. 6, 2018

Related U.S. Application Data

(63) Continuation of application No. 14/821,579, filed on Aug. 7, 2015, now Pat. No. 9,913,570.

(51) Int. Cl.
*A61B 1/00* (2006.01)
*A61B 1/018* (2006.01)
(Continued)

(52) U.S. Cl.
CPC ........ *A61B 1/0008* (2013.01); *A61B 1/00103* (2013.01); *A61B 1/012* (2013.01);
(Continued)

(58) Field of Classification Search
CPC ............ A61B 1/00163; A61B 1/00165; A61B 1/00167; A61B 1/0017; A61B 1/00174;
(Continued)

(56) References Cited

U.S. PATENT DOCUMENTS 4,470,407 A 9/1984 Hussein
5,025,778 A 6/1991 Silverstein et al.
(Continued)

FOREIGN PATENT DOCUMENTS

CN 102137615 A 7/2011
JP 2008538709 11/2008
(Continued)

OTHER PUBLICATIONS

International Search Report and Written Opinion dated Nov. 18, 2016 in Application No. PCT/US2016/045417.
(Continued)

*Primary Examiner* — Ryan N Henderson
(74) *Attorney, Agent, or Firm* — Knobbe, Martens, Olson & Bear, LLP

(57) ABSTRACT

A single-use electronic endoscope has a hub, a shaft extending from the hub, flexible or rigid as desired, and an expandable distal tip extending from the shaft. Within the distal tip, an image sensor provides a field of view external from the endoscope. Illuminating elements or light guides within the distal tip emit light to illuminate the field of view. The distal tip also has a variable profile working channel that permits tools to be passed from the hub and into the field of view. The expandable working channel changes cross-sectional shape from a generally noncircular shape to a shape to accommodate the cross-sectional shape of the tool when expanded.

20 Claims, 8 Drawing Sheets

(51) Int. Cl.
- *A61B 1/05* (2006.01)
- *A61B 1/06* (2006.01)
- *A61B 1/015* (2006.01)
- *A61B 1/012* (2006.01)

(52) U.S. Cl.
CPC .............. *A61B 1/015* (2013.01); *A61B 1/018* (2013.01); *A61B 1/05* (2013.01); *A61B 1/06* (2013.01); *A61B 1/00078* (2013.01); *A61B 1/00082* (2013.01); *A61B 1/00135* (2013.01)

(58) Field of Classification Search
CPC ............ A61B 1/00177; A61B 1/00179; A61B 1/00181; A61B 1/00183; A61B 1/00188; A61B 1/0019; A61B 1/00193; A61B 1/04; A61B 1/042; A61B 1/043; A61B 1/045; A61B 1/05; A61B 1/051; A61B 1/053; A61B 1/055; A61B 1/0071; A61B 1/00078; A61B 1/0008; A61B 1/00082; A61B 1/00119; A61B 1/00121; A61B 1/00128; A61B 1/00135; A61B 1/0014; A61B 1/00142; A61B 1/00154; A61B 1/012; A61B 1/015; A61B 1/018
See application file for complete search history.

(56) References Cited

U.S. PATENT DOCUMENTS

| | | | |
|---|---|---|---|
| 5,090,959 | A | 2/1992 | Samson |
| 5,263,928 | A | 11/1993 | Trauthen |
| 5,464,394 | A | 11/1995 | Miller |
| 5,810,776 | A | 9/1998 | Bacich et al. |
| 6,110,104 | A | 8/2000 | Suzuki et al. |
| 8,038,598 | B2 | 10/2011 | Khachi |
| 8,333,691 | B2 | 12/2012 | Schaaf |
| 8,784,298 | B2 | 7/2014 | Fructus et al. |
| 9,370,295 | B2 | 6/2016 | Kienzle et al. |
| 10,244,928 | B2 | 4/2019 | Konwitz et al. |
| 10,285,571 | B2 | 5/2019 | Rozenfeld et al. |
| 10,582,834 | B2 | 3/2020 | Hastings |
| 10,582,835 | B2 | 3/2020 | Surti et al. |
| 10,588,497 | B2 | 3/2020 | Konwitz et al. |
| 2002/0028986 | A1 | 3/2002 | Thompson |
| 2003/0065318 | A1 | 4/2003 | Pendekanti |
| 2003/0088210 | A1 | 5/2003 | Miskolczi |
| 2004/0003819 | A1 | 1/2004 | St. Goar |
| 2004/0097788 | A1 | 5/2004 | Mourlas |
| 2005/0075711 | A1 | 4/2005 | Neary |
| 2005/0272975 | A1 | 12/2005 | McWeeney et al. |
| 2006/0064059 | A1 | 3/2006 | Gelfand |
| 2006/0184048 | A1 | 8/2006 | Saadat |
| 2006/0235458 | A1* | 10/2006 | Belson .............. A61M 25/0032 606/191 |
| 2008/0058836 | A1 | 3/2008 | Moll |
| 2009/0076331 | A1 | 3/2009 | Konwitz |
| 2010/0063358 | A1 | 3/2010 | Kessler |
| 2011/0054326 | A1 | 3/2011 | Barnett |
| 2011/0092766 | A1 | 4/2011 | Monassevitch et al. |
| 2011/0184233 | A1 | 7/2011 | Fructus et al. |
| 2013/0023920 | A1 | 1/2013 | Terliuc et al. |
| 2013/0053644 | A1 | 2/2013 | Smith |
| 2014/0039253 | A1 | 2/2014 | Fang |
| 2014/0088362 | A1 | 3/2014 | Terliuc et al. |
| 2014/0249569 | A1 | 9/2014 | Kusleika |
| 2014/0378771 | A1 | 12/2014 | St. Onge et al. |
| 2015/0065794 | A1 | 3/2015 | Knight |
| 2015/0150442 | A1 | 6/2015 | Tafti |
| 2016/0095508 | A1 | 4/2016 | Terliuc et al. |
| 2016/0144155 | A1 | 5/2016 | Simpson |
| 2017/0027433 | A1 | 2/2017 | Terliuc |
| 2017/0027458 | A1 | 2/2017 | Glover |
| 2017/0035277 | A1 | 2/2017 | Kucharski |
| 2017/0245737 | A1 | 8/2017 | Truckai et al. |
| 2017/0354318 | A1 | 12/2017 | Rogers et al. |
| 2018/0084971 | A1 | 3/2018 | Truckai et al. |
| 2018/0160893 | A1 | 6/2018 | Truckai et al. |
| 2018/0184892 | A1 | 7/2018 | Truckai et al. |
| 2018/0249888 | A1 | 9/2018 | Kucharski et al. |
| 2018/0326144 | A1 | 11/2018 | Truckai et al. |
| 2018/0333043 | A1 | 11/2018 | Terliuc et al. |
| 2018/0338673 | A1 | 11/2018 | Krimsky |
| 2019/0191983 | A1 | 6/2019 | Terliuc |
| 2019/0254649 | A1 | 8/2019 | Walters et al. |
| 2019/0282078 | A1 | 9/2019 | Terliuc et al. |
| 2019/0380715 | A1 | 12/2019 | Goldin et al. |
| 2020/0164186 | A1 | 5/2020 | Terliuc et al. |
| 2020/0237200 | A1 | 7/2020 | Moktali et al. |
| 2020/0281450 | A1 | 9/2020 | Terliuc et al. |

FOREIGN PATENT DOCUMENTS

| | | |
|---|---|---|
| JP | 201167399 A | 4/2011 |
| JP | 20115297245 | 7/2012 |
| JP | 2014226338 | 12/2014 |
| WO | WO 95/18562 A1 | 7/1995 |
| WO | WO2006/113544 A2 | 10/2006 |
| WO | WO 2013/064060 | 5/2013 |
| WO | WO2017/027299 A1 | 2/2017 |

OTHER PUBLICATIONS

Patel, et al; Interventional radiology-operated endoscopy using the LithoVue disposable endoscope: Approach, technical success, clinical outcomes, and complications; Indian Journal of Radiology and Imaging, Jul.-Sep. 2018; 28(3): 350-353; https://www.ncbi.nlm.nih.gov/pmc/articles/PMC6176675/?report-printable.

Extended International Search Report dated Sep. 18, 2019, in Application No. EP16835655.8; filed Feb. 7, 2018; in 11 pages.

International Search Report dated Nov. 18, 2019 in related International Application No. PCT/US2019/050760; in 16 pages.

IPRP/Written Opinion dated Feb. 13, 2018, in International Application No. PCT/US2016/045417.

Office Action dated May 12, 2020 in International Application No. AU2016304752; Filed Feb. 8, 2018; in 5 pages.

Office Action dated Apr. 23, 2021, in International Application No. AU2016304752; Filed Feb. 8, 2018; in 4 pages.

Office Action dated Jun. 10, 2019, in International Application No. CN201680058679.7; filed Apr. 8, 2018; in 7 pages.

Office Action dated Dec. 25, 2019, in International Application No. CN201680058679.7; filed Apr. 8, 2018; in 10 pages.

Office Action dated Sep. 8, 2020, in International Application No. CN201680058679.7; filed Apr. 8, 2018; in 21 pages.

Office Action dated Mar. 15, 2021, in International Application No. CN201680058679.7; filed Apr. 8, 2018.

Office Action (Rules 161(2)/162 EPC) dated Mar. 18, 2021 in Application No. EP16835655.8; filed Feb. 7, 2018; in 3 pages.

Office Action dated Jun. 24, 2020, in International Application No. JP2018-526491; filed Feb. 6, 2018; in 9 pages.

Office Action dated Dec. 15, 2020, in International Application No. JP2018-526491; filed Dec. 15, 2020; in 7 pages.

Response to May 12, 2020 Examination Report. filed Mar. 25, 2021, in International Application No. AU2016304752.

Response to Mar. 21, 2018 Office Action (161(2)/162 EPC), filed Sep. 28, 2018, in Application No. EP16835655.8.

Response (Rule 70-Prior to examination), filed Apr. 15, 2020, in Application No. EP16835655.8.

* cited by examiner

ENDOSCOPE WITH VARIABLE PROFILE TIP

BACKGROUND OF THE INVENTION

1. Field of the Invention

The described technology relates generally to devices and methods for imaging within a body lumen, cavity or other enclosed space, and, more particularly, it relates to a single-use electronic endoscope for various uses (e.g., for arthroscopic knee surgery).

2. Description of the Related Art

Diagnosing and treating patients often involves examination of internal organs and structures. In "open surgery," a large surgical cut or incision is made in the patient's skin and flesh. Doing so permits the doctor to see directly into and access the area being treated. However, large surgical wounds cause significant patient pain, involve use of powerful anesthetics and analgesics such as narcotics to keep the patient comfortable during and after surgery, often take significant time to heal and limit post-surgical patient activity (particularly if muscle is cut to access the treatment area).

To avoid disturbing nearby tissues, doctors use various imaging technologies to probe ducts, orifices, bodily openings, or other spaces. Such devices allow remote viewing of difficult-to-access spaces without large incisions, and have been referred to by different names, including angioscope, arthroscope, borescope, cystoscope, endoscope, and fiberscope.

Arthroscopy is increasingly popular. Common arthroscopic procedures examine and treat damaged tissue within various body joints, such as by removal or repair of torn cartilage portions of the meniscus, ligament, and tendon reconstruction, removal of loose debris, and trimming or shaving damaged articular cartilage. More than 4 million knee arthroscopies and more than 1.4 million shoulder arthroscopies are performed worldwide each year, according to the American Orthopedic Society for Sports Medicine. Other joints such as the shoulder, elbow, ankle, hip, and wrist can also be viewed through arthroscopy.

An endoscope has a light source and a camera. Fiberscopes (or fiber-optic endoscopes) include both illumination fibers or light guides to direct light which illuminates the field of view and imaging fiber bundles to transfer the image of an illuminated area to the camera. In diagnostic arthroscopy, after introducing the device into the patient's joint, the doctor shines light into that joint. The camera provides an image of the joint, which is then viewed on a video monitor. By viewing the joint of interest through the device, the doctor does not need to make a large incision. Sterile fluid can be used to expand the joint, which increases visibility in the joint area and makes it easier for the doctor to work. These single-port diagnostic procedures have been performed in a doctor's office and "walk in" or ambulatory surgery centers, e.g., using a 2.0 mm fiber optic arthroscope. Routinely these diagnostic procedures are performed under local anesthetic to numb the area being examined and the patient remains awake throughout the procedure.

Other endoscopes are used to actively treat or operate on patients' joints. The doctor inserts the endoscope into the joint. Additional holes or incisions can be provided to allow other tools to be used during the surgery to cut, shave, remove particles in the joint, or repair tissue. Alternatively, the endoscope can include a working channel that allows surgical tools (e.g., biopsy forceps and other tools) to slide in and out of the joint.

Such operative or therapeutic arthroscopic surgery has limitations. Operative endoscopes with working channels for arthroscopy are typically 3-4 mm in diameter. This makes the overall procedure more invasive and more taxing on the patient than when smaller diagnostic endoscopes are used.

Operational arthroscopic procedures can have life-threatening risks. General anesthesia, with its attendant risks, can be used, particularly for more interventional operative arthroscopy. To avoid accidental patient infection, doctors use sterile techniques and equipment.

Such risks are not trivial. The Ronald Reagan UCLA Medical Center is a leader in performing the latest minimally invasive endoscopic procedures. In February 2015, as many as 179 people at that hospital were exposed to drug-resistant bacteria while undergoing endoscopic procedures. According to press reports, seven of those people become infected with methicillin-resistant *Staphylococcus aureus* (MRSA), and two of those patients died.

The U.S. Food & Drug Administration issued a general warning to all health providers regarding the use of medical endoscopes for complex endoscopic procedures. The complex design of some endoscopes impedes the ability to clean, disinfect, and sterilize these reusable devices.

Previously known endoscopes suffer a number of disadvantages, including significant initial cost and the need for sterilization after each use. Such sterilization procedures are time consuming and lead to further expense.

U.S. Pat. No. 6,840,909 to Gatto describes a device for removal of tissue and cells from breast ducts. At its distal end, the device has a rigid or semi-rigid cannula tube. This cannula has an outer diameter ranging from 0.5 mm to approximately 1.2 mm, and acts as a guide tube for an endoscope. To obtain biopsy cells and tissue, a physician manipulates the cannula tube itself to scrape cells free of tissue. Injecting saline into the area followed by application of a vacuum withdraws the water and scraped cells from the patient.

U.S. Pat. No. 8,323,181 to Mukherjee describes an endoscope with an insertion end that is about 1 to 2 mm in outer diameter. FIG. 5 shows the tip of the insertion end of the endoscope, which has a flexible polyamide sheath. Enclosed within the sheath are an image-bundle focus lens, two laser-focus lenses, and optical fiber bundles used for illumination.

U.S. Pat. No. 8,858,425 to Farr describes an endoscope with removable, pluggable, and disposable optoelectronic modules. FIG. 7b shows a surgical tool 750 that can be inserted through the disposable cannula 700 after the distal end 702 has been inserted inside the body. That distal end 702 is made flexible so that, after insertion into the patient, the entire distal tip 702 of the cannula can be expanded radially.

SUMMARY OF THE INVENTION

This is a general summary of the described technology commensurate in scope with the original claims. This technology overcomes disadvantages of the previously known operative endoscopes, and provides a single-use or disposable, low-cost, electronic endoscope with a variable profile distal tip. The technology encompasses various forms similar to and different from the specific modes for implementing the inventions (also called "embodiments") described below.

These described endoscopes are intended to provide a brief summary of some possible forms of the technology, and are not intended as a comprehensive disclosure of the full scope or all of the features of the described technology and do not limit the scope of the attached claims.

In one aspect, an electronic endoscope has a hub. A shaft extends from the hub. An expandable distal tip extends from the shaft. An image sensor within the distal tip has a field of view external from the endoscope. A light source within the distal tip emits light within the image sensor's field of view.

Tools can be passed from the hub, along the shaft within a working channel, and to the distal tip. A variable profile working channel at the distal tip allows one or more tools to pass the image sensor and into its field of view without increasing the overall size of the endoscope at the proximal shaft. The working channel changes from a relatively compact, generally noncircular cross-sectional shape to a different and enlarged cross-sectional shape. This shape change accommodates tools passing through the working channel, but also allows the endoscope to have a relatively low profile when first inserted into the patient.

In another aspect, a single-use endoscope with a distal tip has a hub portion enclosing a light source and an insertion portion (that portion capable of being inserted into the patient's body) extending from the hub portion. The insertion portion includes an expandable outer sheath at the distal tip of the endoscope. A light transmission system within the insertion portion conveys light from the light source and projects that light from the distal tip and onto a subject to be illuminated. An image sensor, located approximately at the center of the distal tip, picks up an image of the illuminated subject.

A variable profile working channel extends from the hub portion to the distal tip of the endoscope. A low-profile or reduced-profile configuration of the working channel fits within at least a portion of space defined between the image sensor and the expandable outer sheath. An enlarged-profile configuration has a cross-sectional shape sufficient to allow tools to pass the image sensor and to extend out from the endoscope's distal tip. When the working channel is in the enlarged-profile configuration, the expandable outer sheath has a generally noncircular shape at the distal tip.

In a further aspect, an endoscope has a proximal end, a distal end, and a field of view at its distal end. A hub is at or near the proximal end. An insertion portion extends from the hub towards the distal end. An expandable distal tip extends from the insertion portion to the distal end and has a sensor. The sensor picks up an image within the field of view. A working channel, a flushing lumen and a light-guide extend within the insertion portion from the hub to the distal end. At a point along the insertion portion, the endoscope has a cross-section with the flushing lumen, the light-guide, a generally circular cross-section of the working channel and a cable extending from the sensor to the hub.

The cross-section differs at another point along the distal tip. This second cross-section has the sensor, the working channel, the flushing lumen and the light-guide. Both the working channel and the flushing lumen in this second cross-section have independently variable profiles. Each transforms from a generally noncircular, low-profile configuration to an enlarged-profile configuration. The enlarged-profile configuration allows one or more tools to pass through the working channel or permits liquid to travel through the flushing lumen.

These endoscopes are capable of many variations. For example, the ratio of the length of the endoscope portion with the expandable or elastomeric working channel (1) to the outer diameter of the insertion portion (D) ranges from about 5:1 to about 1:1, and preferably is less than about 4:1, and most preferably less than about 2:1.

In at least some of the disclosed endoscopes, the expandable working channel assumes the enlarged-profile without moving the image sensor relative to the light transmission system. For example, the expandable distal tip can have an elastomeric sheath, which assumes a generally noncircular cross-sectional shape when either the working channel or the flushing lumen is enlarged. In other disclosed endoscopes, the camera moves slightly in one direction while the tip expands to allow a tool to pass. Once the tool emerges and expansion is done, the camera can be repositioned. Having passed the camera, the tool can be pushed forward or back with a range of motion that does not cause further camera movement.

The expandable outer sheath, the flushing lumen and the variable profile working channel can be made from various sterilizable, biocompatible polymeric materials. Each can be made from materials having biocompatible elastomeric tubing, which can be the same materials or different materials. In addition, the flushing lumen and the variable profile working channel can also be made from biocompatible non-elastomeric materials. The enlarged working channel is capable of accommodating passage of a tool having a circular cross-sectional shape with a diameter equal to at least 50% of the outer diameter of the insertion portion (D), preferably equal to at least 60% of D, and most preferably equal to at least 95% of D. When either the flushing lumen or the working channel is enlarged, the outer sheath assumes a generally noncircular cross-sectional shape.

The described electronic endoscopes are useful for various operative or therapeutic procedures (e.g., arthroscopy, gall stone intervention, gynecologic endoscopy, kidney stone intervention, otolaryngologic endoscopy, and urologic endoscopy). Such disposable endoscopes do not need re-sterilization, and can provide good visualization in a relatively small package, because the portion of the endoscope inserted into the patient has an outer diameter of about 2 mm or less. This facilitates therapeutic endoscopic use by general practice doctors in their offices on an outpatient basis and avoids delays and costs associated with scheduling procedures to occur in hospital operating rooms.

Methods of assembling and using these endoscopes also are provided.

The technology has been briefly described thus far. This Summary introduces select concepts in a simplified form, which are further described throughout this application, including in the Detailed Description of the Preferred Embodiments. This Summary is neither intended to identify key or essential features of the claimed subject matter, nor intended to be in any way limiting of the scope of the claims attached hereto. The features mentioned above and those yet to be explained below can be used not just in the stated combinations, but also in other combinations, or alone, without departing from the scope of this application. In addition to the illustrative aspects, embodiments, and features described above, a more complete understanding will be afforded to those skilled in the art, as well as a realization of these and other objects, features and advantages of the described technology by consideration of the following text and the accompanying illustrative drawings.

BRIEF DESCRIPTION OF THE DRAWINGS

To illustrate the described technology and otherwise clarify the above and other features and advantages of the technology, descriptions that are more particular are provided below by reference to specific embodiments illustrated in the accompanying illustrative drawings. These drawings depict selected modes of the described technology and are not to be considered limiting of its scope. The technology will be described and explained with additional specificity and detail through the use of these drawings, in which like reference numerals refer to like parts throughout, and in which:

FIG. 2b is a cross-sectional view of the expandable tip of FIG. 1 taken along a section of FIG. 2a;

Figure 1:
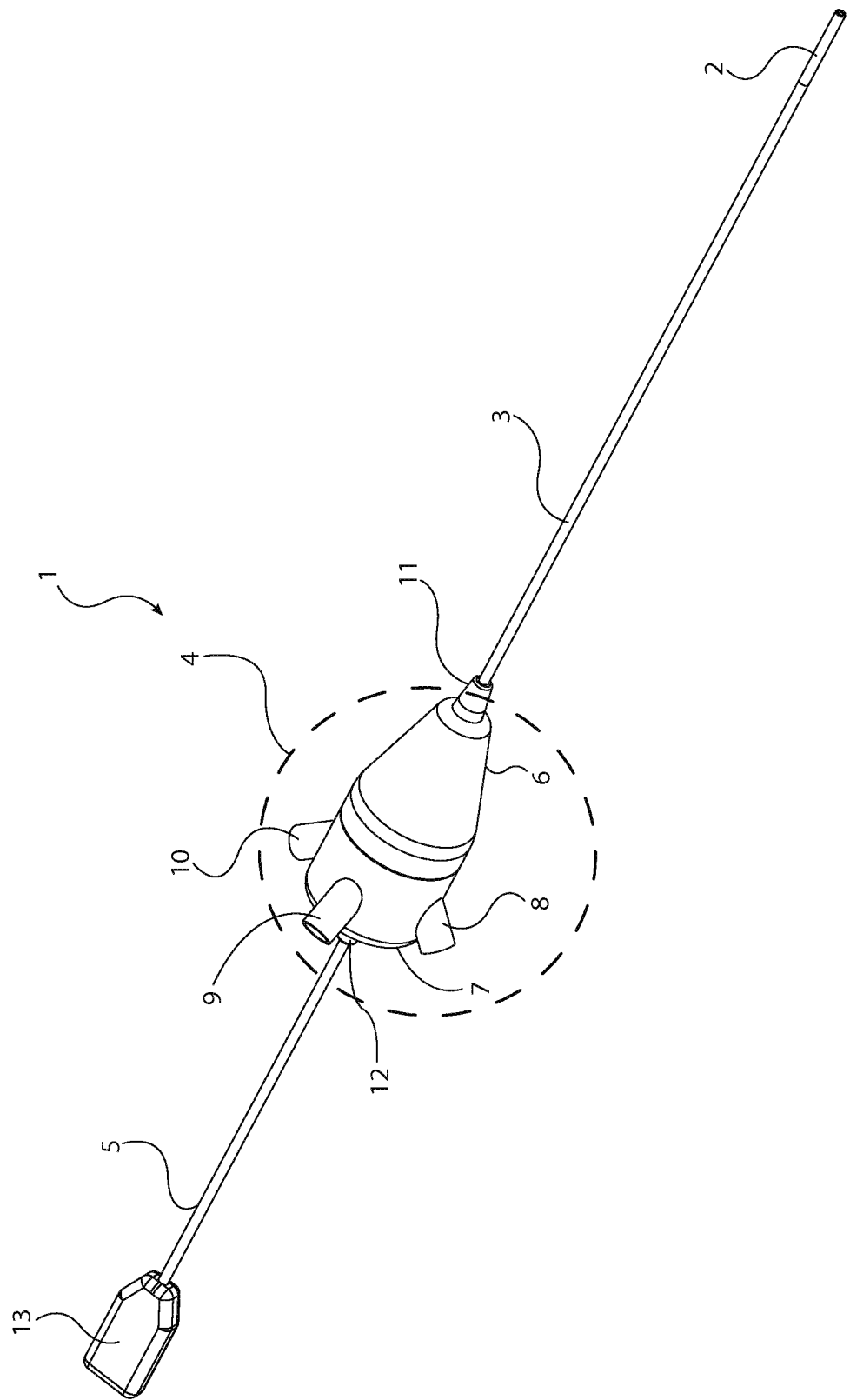
FIG. 1 is a schematic view of an illustrative endoscope constructed in accordance with the principles outlined in this application.

The provided drawings are illustrative and this technology is not limited to the precise arrangements shown. The described technology can be carried out in a variety of other ways, including those not depicted in the drawings. The drawings and angles of the disclosure are not always to scale so as to clearly portray the attributes of the technology, are intended to depict typical aspects of the disclosure, and should not be considered as limiting the breadth, scope or applicability of the described technology. Additional features and advantages of the described technology are set forth in, and will be apparent from, the following Detailed Description of the Preferred Embodiments.

DETAILED DESCRIPTION OF THE PREFERRED EMBODIMENTS

Various exemplary aspects of the described technology are illustrated in the Figures and discussed below, which are presented to enable the manufacture and use of various aspects and examples of that technology. Descriptions of specific materials, techniques, and applications are provided as examples. No limitation on the scope of the technology and of the claims that follow is to be imputed from the drawings, the examples, or the discussion below.

This application provides an electronic endoscope with a variable profile tip, in particular a single-use or disposable, low-cost, electronic endoscope with a variable profile working channel.

In one endoscope, the electronic endoscope has a hub, which remains outside the patient's body. The hub is used by the doctor to manipulate the endoscope. An elongated, flexible shaft extends from that hub. This is the portion of the endoscope, that can be inserted into the patient's body. An expandable tip extends from the end of the shaft that is farthest away from the hub. This is the distal tip. This expandable distal tip has sensors that allow the doctor to see inside the patient's body and a working channel, which allows the doctor to treat or operate on nearby structures. In particular, a complementary metal oxide semiconductor (CMOS) image sensor is positioned within the distal tip and has a field of view external from the endoscope, although other sensors can also be used. One or more illuminating fibers within the distal tip emit light within the image sensor's field of view.

The distal tip has a variable profile working channel. The working channel permits one or more tools (e.g., ablation devices, cannulas, dissectors, electrodes, forceps, graspers, knot pushers, laser fibers, needle holders, suction and irrigation instruments, trocars, and other tools) to be passed within the endoscope from the hub to the image sensor's forward field of view. The variable profile working channel can change shape to allow the tools to pass alongside the image sensor. For example, the expandable working channel can change from a generally noncircular cross-sectional shape to a different and enlarged cross-sectional shape which permits tools to pass.

Another endoscope has a hub that encloses a light source. The doctor uses the hub to manipulate the endoscope. An insertion portion extends from the hub. At the distal tip of the endoscope (furthest from the hub), the insertion portion has an expandable outer sheath. A light transmission system conveys light from the hub and onto a subject to be illuminated beyond the distal tip. An image sensor is positioned at approximately the center of the endoscope's distal tip. The sensor picks up an image of the illuminated subject.

A variable profile working channel extends from the hub to the distal tip of the endoscope. The working channel is positioned inside the expandable outer sheath. A low-profile configuration of the working channel fits within a space defined between the image sensor and the expandable outer sheath. An enlarged-profile configuration of the working channel permits tools to travel past the image sensor and out of the distal tip. When the working channel is in the enlarged-profile configuration, the expandable outer sheath has a generally noncircular shape at the distal tip.

A further endoscope has a proximal end closest the doctor, a distal end at the opposite end and a field of view at that distal end. The hub is at the proximal end. The portion of the endoscope which extends from the hub towards the distal end can be termed the "insertion portion." Depending on the doctor's needs, some or the entire insertion portion can be inserted into the patient. The hub remains outside the patient.

An expandable distal tip extends from the insertion portion to the distal end and has a sensor configured to pick up an image within the field of view. A working channel, a flushing lumen, and a light-guide (e.g., one or more optical fibers) extend within the insertion portion from the hub to the distal end. At a point along the insertion portion, the endoscope has a cross-section, which includes the flushing lumen, the light-guide, a generally circular cross-section of the working channel, and a cable extending from the sensor to the hub.

At a different point along the distal tip, the endoscope has a different cross-section. That different cross-section has the image sensor, the working channel, the flushing lumen, and the light-guide. Both the working channel and the flushing lumen are capable of changing their profiles, and are capable of doing so independently of one another. Each can assume a generally noncircular, low-profile configuration. Each can also assume an enlarged-profile to accommodate a tool passing through the working channel or to accommodate liquid passing through the flushing lumen.

Each of the endoscopes described briefly above has an expandable distal tip, a variable profile working channel and, optionally, an expandable flushing lumen. The materials from which these three structures are made can be the same or different. Biocompatible elastomeric material can be used to make all three structures (e.g., silicone rubber, thermoplastic elastomer (TPE)). TPEs include copolyester elastomers (e.g., ARNITEL® from DSM), polyether block amide (e.g., PEBAX® from Arkema), polyether polyester block copolymers (e.g., HYTREL® from Du Pont), polyolefin elastomers (e.g., ENGAGE® from Dow Chemical), polyurethane elastomer (e.g., PELLETHANE® from Dow Chemical), styrene block copolymers (e.g., EVOPRENE® from AlphaGary), styrene-butadiene block copolymers (e.g., STYROFLEX® from BASF), styrene-ethylene-butylene-styrene block copolymers (e.g., KRATON® from Kraton Polymers), and thermoplastic vulcanizates (e.g., SANTOPRENE® and GEOLAST® from ExxonMobil).

The working channel and the optional flushing lumen also can be made from non-elastomeric materials, which can change from a low-profile configuration to an enlarged-profile configuration (e.g., poly(ethylene-vinyl acetate) (PEVA), polyimide, polytetrafluoroethylene (PTFE), or polyvinyl chloride (PVC)). Relatively rigid tools pass through the working channel, which can benefit from a more durable, rugged polymeric material, while the distal tip needs to accommodate the enlarged working channel and/or enlarged flushing lumen.

Referring now to FIG. 1, an endoscope 1 has an expandable tip 2, a shaft 3, a coupling hub 4, a connector assembly 5, and a USB connector 13. The endoscope 1 shown has an overall working length (combined length of the shaft 3 and the distal tip 2) of between 5 cm and 200 cm, preferably between to cm and 100 cm, and most preferably between 12 cm and 600 cm. The working length should be sufficient to allow the tip of the endoscope 1 to be positioned within the patient's body so that the relevant anatomy can be seen, while maintaining the coupling hub 4 outside the patient's body.

The shaft 3 extends from the distal tip 2 to the coupling hub 4. The shaft 3 transmits torque (rotation) applied about a longitudinal axis of the shaft 3. Torque applied to the proximal end of the shaft is transferred along the length of the shaft 3 and to the distal tip 2. In some endoscopes, the shaft 3 is flexible and can be bent about a transverse axis of the shaft in a relatively small bend radius. This allows the endoscope to be maneuvered around anatomical structures during medical procedures. However, in other applications, some or the entire shaft 3 is rigid or semi-rigid.

The shaft 3 can be made from any biocompatible material with appropriate strength characteristics (e.g., providing flexibility and strength in tension and compression, as well as appropriate torque transfer from the proximal to the distal end). Materials from which the shaft 3 can be made include biocompatible polyamides, polyesters, polyetheretherketones, polyetherurethanes, polyimides, polytetrafluoroethylene, and polyurethane epoxies. To provide additional strength or rigidity, reinforcing materials can be incorporated into the shaft 3. Such reinforcing materials include copper alloys, nickel alloys (e.g., Nitinol), stainless steel, and high modulus plastics such as polyimides.

The coupling hub 4 contains one or more connectors 8, 9, 10 for tools, flushing fluid, and a stylet, as well as optional electronics. The coupling hub 4 has a size and shape which accommodates these components. Electronics within the coupling hub 4 include a PCA with circuitry to operate the endoscope and a camera signal transmission system that are discussed below. Alternatively, the PCA can function as an interconnection to external control circuitry outside of the endoscope. If electronics internal to the hub 4 are not otherwise desired, the hub 4 can be quite small and can serve as a connection joint between the other tubes, wires, and optical fibers.

The hub 4 is made of a biocompatible plastic, such as polycarbonate, acrylic, acrylonitrile butadiene styrene (ABS), cast epoxy, and thermoset plastics. Formed metal housings using biocompatible materials, such as several grades of stainless steel or titanium, are also possible.

The coupling hub 4 has a distal portion 18 and proximal portion 19. The coupling hub 4 includes one or more ports or connectors 8, 9, 10, and strain relief features 11, 12. These connectors 8, 9, 10 include seals to provide fluid tight seal between coupling hub 4 and the connectors 8, 9, 10 (e.g., a LUER-LOK® lock component).

The connectors 8, 9, 10 attach firmly to the coupling hub 4 and allow doctors to introduce tools and fluids at the hub 4 that can be used at the distal tip 2 of the endoscope. This can be achieved by gluing, heat-welding, potting with thermoset plastic or epoxy, RF welding, screwing them on with a threaded connection, solvent bonding, ultrasonic welding, or combinations of these processes. Any or all of these three connectors 8, 9, 10 can be attached to a flexible tube, which enters the hub 4.

The flushing channel connector 8 allows fluid to be introduced at the hub 4, which can travel through the flushing lumen 24. The stylet channel connector 9 allows for a stylet (not shown) to be inserted at the hub 4 and into the stylet channel 27. The stylet is intended to influence the shape of the endoscope's flexible shaft 3. For example, a malleable and resilient wire made of materials such as 300-series stainless steel can be bent into a desired curvature or angle, and inserted through the stylet channel causing the flexible endoscope to conform to such curvature or angle. The working channel connector 10 allows tools to be passed from the hub 4 through the working channel 28, within the shaft 3, and down to the working channel portion 23 within the distal tip 2.

Although the endoscope shown has a single variable profile working channel, it is contemplated that more than one working channel can be included. When multiple working channels are employed, they may be the same size or different sizes. Some or all of the working channels can have the variable profile feature. For example, a 5 mm endoscope could have two 1.2 mm working channels, both of which have the variable profile feature.

Similarly, FIG. 1 shows three connectors 8, 9, 10 for the flushing lumen, stylet, and working channel, respectively. It is contemplated that as few as one connector could be used, or as many connectors as needed for the flushing lumen, stylet, and working channel features of the particular endoscope. For example, an endoscope with two working channels, a stylet, and a flushing lumen could have four separate connectors.

The electrical cable 5 and USB connector 13 provide an interface between circuitry within the coupling hub 4 and external devices. In FIG. 1, a single cable 5 extends from the coupling hub 4 to the USB connector 13. This cable 5 has conductors for powering a light source within the coupling hub 4 and has contacts for transmitting signals outputted by the camera 22 to the USB connector 13. Multiple cables can be used with, for example, a first cable 5 conducting power to a light emitting diode (LED) light source in the coupling hub 4, and a separate second cable (not shown) transmitting signals receives from the camera 22.

The USB connector 13 connects to external control/display devices or into an electronic interface box, which translates the USB signals into those used by the external control or display devices. The USB connector 13 also provides power for the electronic endoscope. Although a USB connector is shown in FIG. 1, other wired connections (e.g., HDMI) and wireless connections (e.g., Bluetooth, WiFi) are also possible as discussed below.

The coupling hub 4 undergoes various forces during use, including bending forces. Strain relief features 11, 12 protect the hub 4 and its components from these forces. For example, FIG. 1 shows a distal strain relief 11 and a proximal strain relief 12. Strain relief features 11, 12 can be made from various materials. These include relatively hard injection molded thermoplastics (e.g., acrylonitrile butadiene styrene (ABS)), or more flexible materials such the TPEs previously identified. When a TPE is used, it preferably has a higher durometer value than the expandable tip components.

Figure 2A:
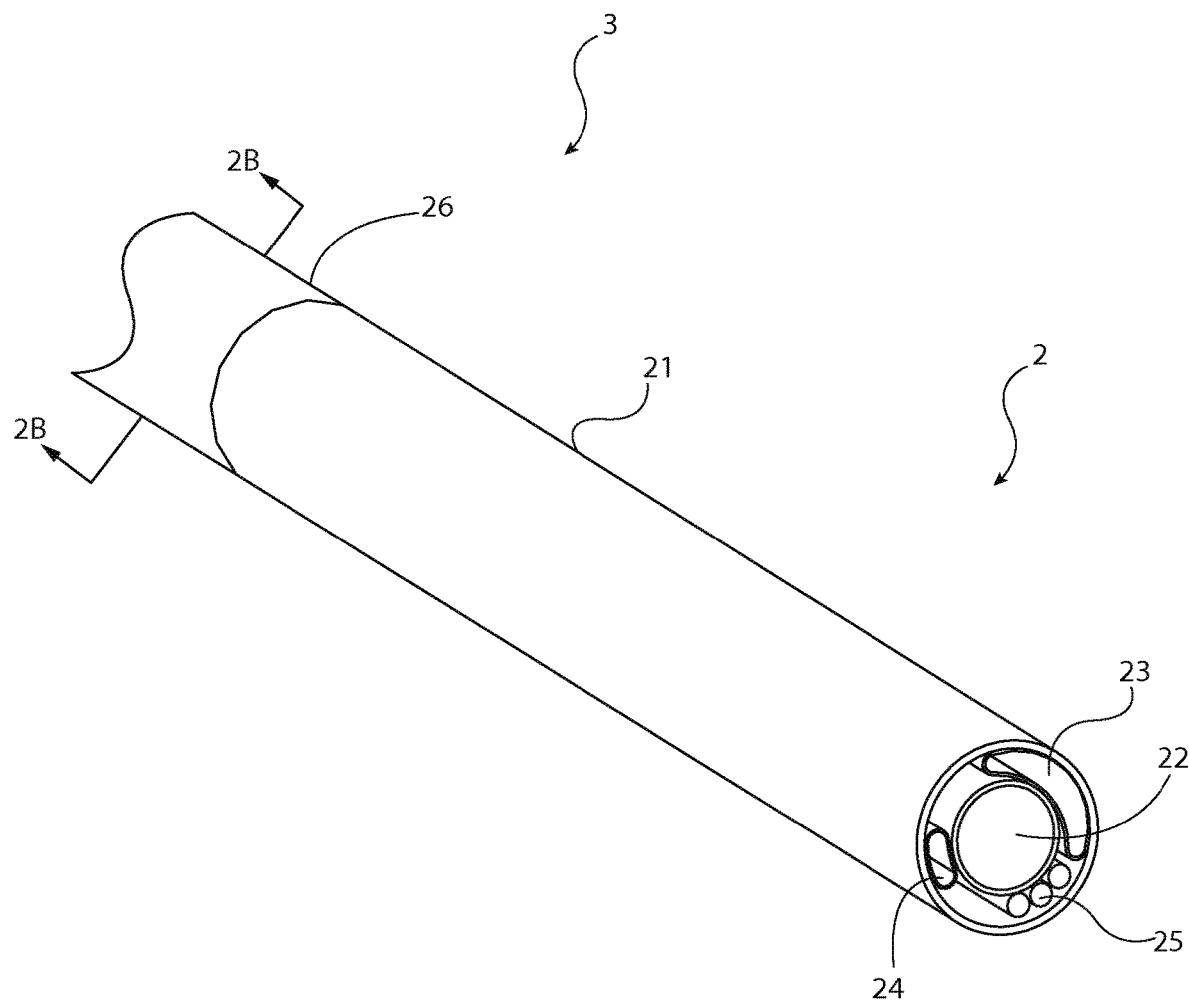
FIG. 2a is a perspective view of the expandable tip in the non-expanded configuration of the endoscope of FIG. 1.
Figure 2B:
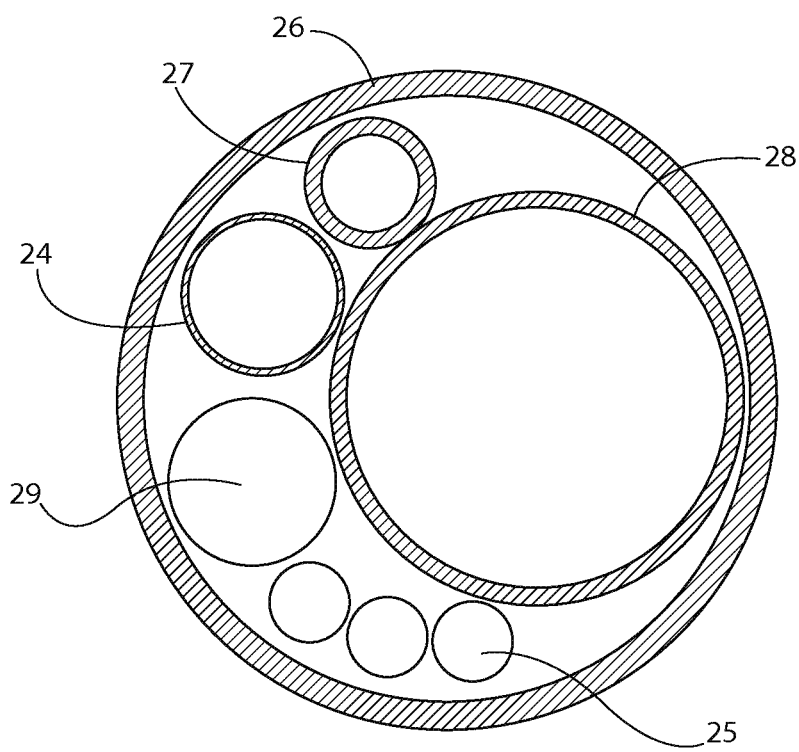

FIGS. 2a and 2b show the distal end of the endoscope 1 in both perspective and cross-sectional views. In FIG. 2a, the expandable tip 2 has an expandable outer cover 21. At the distal end, the structure within the expandable tip 2 is shown, and includes a variable profile working channel 23, an expandable flushing channel 24, three illumination fibers 25, and a camera 22. The distal tip 2 is long enough to house the camera 22. For example, the distal tip 2 has a length from the end of the shaft 3 to the distal most part of the endoscope of between 3 mm and 50 mm, preferably between 7 mm and 15 mm, and most preferably between 8 mm and to mm.

The distal tip 2 can enlarge and contract. In a low-profile state, the distal tip 2 has a reduced cross-sectional area with an outer diameter of between about 1.5 mm and 20 mm, preferably between about 1.5 mm and 5 mm, and most preferably between about 1.5 mm and about 2.0 mm. In an enlarged-profile or expanded state, the distal tip 2 has an enlarged cross-sectional area that will accommodate passage of one or more tools through the working channel. For example, the enlarged-profile accommodates passage of a tool having a circular cross-sectional shape with a diameter of between 1.8 mm and 20 mm, preferably between 2 mm and 5 mm, and most preferably between 1 mm and 2 mm. The profile change allows tools to pass the camera 22, and ultimately to exit the distal tip of the endoscope.

The illumination fibers 25 are depicted as three flexible fiber-optic light-guides. These fibers 25 carry light from a light source in the coupling hub 4 to the distal tip 2 of the endoscope, illuminating a field of view. Although three fibers 25 are shown in FIG. 2A, as few as one fiber can be used or as many fibers as can fit within the allowable space so long as they provide sufficient light for camera 22. Illumination fibers 25 can be made of glass, PMMA or other light transmitting materials. Combinations of different sized fibers 25 can be used, as long as they fit within the cross-sectional area of the distal tip 2 in its low-profile configuration and provide sufficient illumination intensity.

The camera 22 and illumination fibers 25 are positioned so the area to be imaged is sufficiently illuminated. In the configuration shown, the camera 22 can be approximately in the center of the distal tip 2, with the working channel 23, the flushing lumen 24 and the illumination fibers 25 angularly distributed around the circumference (e.g., the working channel 23 separated by about 120° from the flushing lumen 24 and by an equal amount from the illumination fibers 25). However, various locations of the working channel 23 and flushing channel 24 relative to each other and relative to the camera 22 or the illumination fibers 25 are possible.

The outer cover 21, the working channel 23, and the flushing channel 24 are made of sterilizable polymeric materials. Within at least the expandable tip portions, these structures are configured so that they can change shape or expand. Each of these structures can be made from the same material, or the materials can be different. For example, each can be constructed of biocompatible elastomeric tubing (e.g., latex rubber, silicone rubber, or various USP Class 6 compatible TPEs). Exemplary TPEs are mentioned above.

In a single-use endoscope, sterilization by the original manufacturer can be done in bulk (e.g., using ethylene oxide gas, gamma radiation, steam). A single-use device can have tubing connections that butt against one another but still allow a small crack, gap, or void at the joint. Materials suitable for the bulk sterilization, such as by ethylene oxide gas, can also be used to construct the endoscope without concern for the materials having to be compatible with multiple exposure to sterilization chemicals such as glutaraldehyde.

Coatings (not shown) can be applied to the outside of the endoscope. For example, such coatings could provide anti-bacterial or anti-microbial properties (e.g., copper ions, silver ions). Coatings can also be used to allow doctors to detect certain conditions. For example, special peptides and other formulations can be applied that detect presence of bacterial contamination or biomarkers of other sorts.

To seal the distal tip of the endoscope, a UV-cured adhesive potting compound is applied at the distal tip and flows between the components, while it is viscous. Excess potting compound is removed and UV light applied to cure or harden the material. Other materials can also be used, such as 2-part epoxies. Application of the potting compounds may be limited to areas that do not interfere with the expandable distal tip sections (e.g., by fixtures that limit the distribution area of the compound), and/or use materials that do not bond to those expandable sections.

The working channel 23 has a low-profile configuration. For example, the low-profile working channel 23 of a 2 mm endoscope can have a 0.5 mm diameter within the shaft 3 and then assumes a more compact configuration within the distal tip 2 so that it fits the space between the expandable outer cover 21 and the camera 22. In FIG. 2a, the low-profile working channel 23 has a generally lunate cross-sectional shape. The ends of the lunate cross-sectional shape can be rounded (as in FIG. 2A), or bent more sharply. Other shapes are possible, including circular, reniform, oblong, oval, etc.

The working channel 23 also has an enlarged-profile configuration to allow tools to pass the camera 22. For example, the enlarged-profile working channel 23 of 2 mm endoscope is large enough to allow tools with an outer diameter of approximately 1.2 mm to pass through it.

The camera 22 is a CMOS color camera, which is biocompatible and waterproof. Preferably, the camera provides a field of view external from the endoscope. A forward field of view would look beyond the distal tip of the endoscope. However, the field of view can also be at an angle external from the endoscope (e.g., an off-angle-looking endoscope such as 30°). The CMOS image sensor includes a multi-element lens assembly or gradient refractive index (GRIN) lens providing a field of view of 30-180°, preferably of 50-130°, and most preferably 60-120°. The effective image resolution preferably is at least 10,000 pixels, more preferably at least 40,000 pixels, and most preferably at least 60,000 pixels, although image resolutions of 1 megapixel or greater are possible. Other sensors can be used instead of or in conjunction with the CMOS device so long as they provide sufficient image resolution. For example, a charge-coupled device (CCD) could be used.

Optionally, an optical prism can be added to modify the particular angular view of the image sensor. The prism has a reflective surface that "tilts" the viewing cone of the image sensor by a predetermined amount, such as 30°, 70°, etc. The prism may be made of glass or any clear polymer, such as acrylic or polycarbonate. The prism could be bonded using optically-clear epoxy to the flat distal surface of the camera. More preferably, the prism could replace the final camera lens in the original manufacture of the device.

The camera sensor can be further affixed to the structure of the endoscope. The camera sensor can be affixed directly to the light guide to provide additional support. The camera cable can be adhered to the sheath cover, the working channel, or both. For example, the camera cable can be bonded to the inside of the sheath cover, just proximal to the expandable distal tip section. These further connections provide added stiffness.

The cross-sectional view of FIG. 2b is along section A-A of FIG. 2a, and passes through the elongated shaft 3. A flexible, braided sheath cover 26 is made from a stainless steel reinforced polyimide material, although other materials can be used.

The braided sheath cover 26 contains five structures. The working channel 28 in this section is a flexible tube with a generally circular cross-sectional shape. The working channel 28 can be constructed from any sterilizable polymeric material than can be affixed to the variable profile working channel 23 shown in FIGS. 1 and 2a, or working channel 28 and variable profile working channel 23 can made from the same length of tubing. The material of working channel 28 can be the same material as that of variable profile working channel portion 23, or they can be made from different materials. For example, the working channel within the shaft 3 can be made from non-elastomeric polymeric materials (e.g., poly(ethylene-vinyl acetate) (PEVA), polyimide, polytetrafluoroethylene (PTFE), polyvinyl chloride (PVC)) or from biocompatible elastomeric tubing (e.g., latex rubber, silicone rubber, or various USP Class 6 compatible TPEs).

Figure 3:
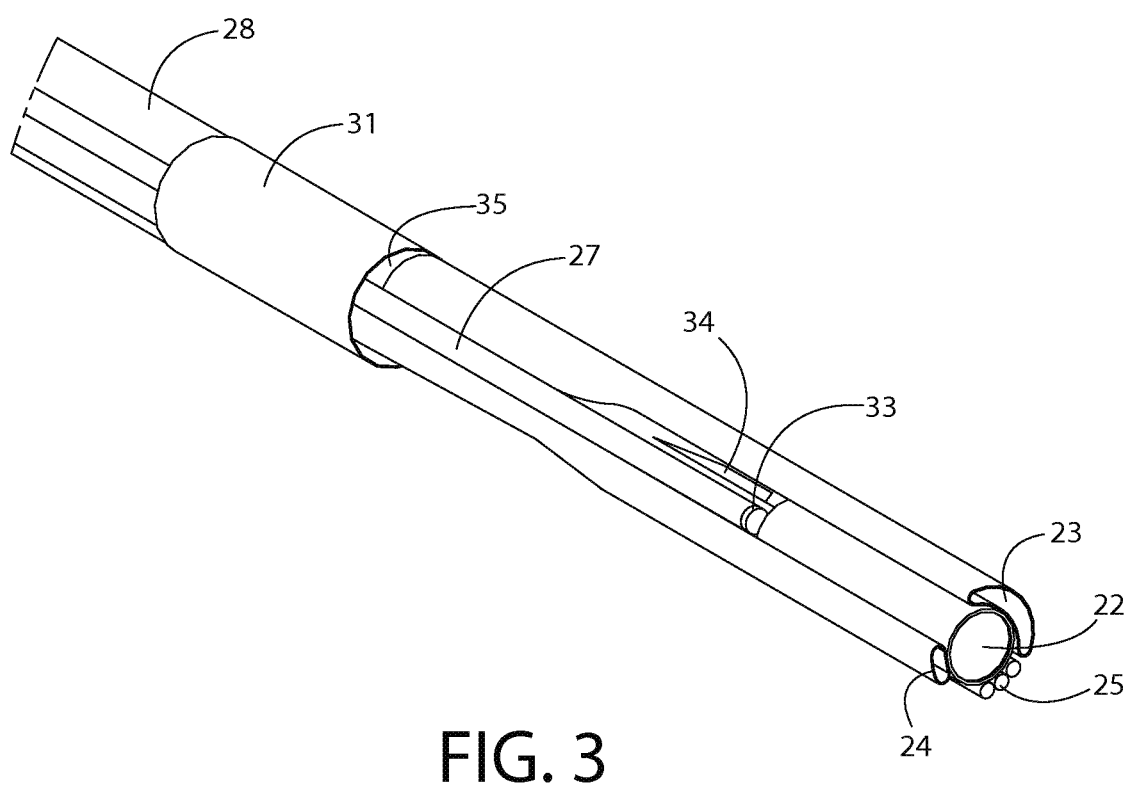
FIG. 3 is a view of the non-expanded tip components of the endoscope of FIGS. 2a and 2b underneath the outer cover sheaths.

Flushing fluid passes through the flushing channel 24. The flushing channel 24 can have any cross-sectional shape within the shaft 3 so long as sufficient fluid can be passed. The flushing channel 24 shown in FIG. 3 is made from a single length of elastomeric tubing. Alternatively, the proximal portion of flushing channel 24 within the shaft 3 can be made from non-elastomeric material (e.g., a polyimide tube) and coupled to an elastomeric tip section. Suitable elastomeric materials for the flushing channel 24 are identified above.

A stylet channel 27 allows introduction into the endoscope of a stylet (not shown), which is a slender probe, typically made from a metal. When the stylet is introduced, it provides additional stiffness. This can facilitate proper positioning of the endoscope's distal tip within the patient. In addition, the stylet can impart a particular shape to the endoscope (e.g., a particular curve or bend). The stylet channel 27 should resist puncture by the stylet tip. Reinforcement is optional. This stylet channel 27 is made from various polymeric tubing materials, such as PEVA, polyimide, PTFE, or PVC. The stylet channel 27 is shown to have a circular profile, but can have any profile that allows the stylet to pass through it.

Also, a camera cable 29 extends from the camera 22 (shown in FIG. 2a) to the coupling hub 4 (shown in FIG. 1). The camera cable can be a simple signal conducting wire (e.g., a 24 AWG gauge copper wire with a diameter of about 0.52 mm), or a ribbon cable with several insulated conductors. Exemplary conductor compositions include copper, copper alloys, MP35N, DFT, platinum, platinum/iridium, tungsten, gold, and stainless steel. The conductors can be bare, tinned, silver-plated, or gold-plated. Various insulating materials can be used, including fluorinated ethylene propylene (FEP), perfluoroalkoxy (PFA), and polytetrafluoroethylene (PTFE). For example, the ribbon cable can be constructed with four conductors: (1) a ground, (2) a serial data line, (3) a serial clock line, and (4) a power line (e.g., using 41 AWG silver plated copper conductors).

Figure 2C:
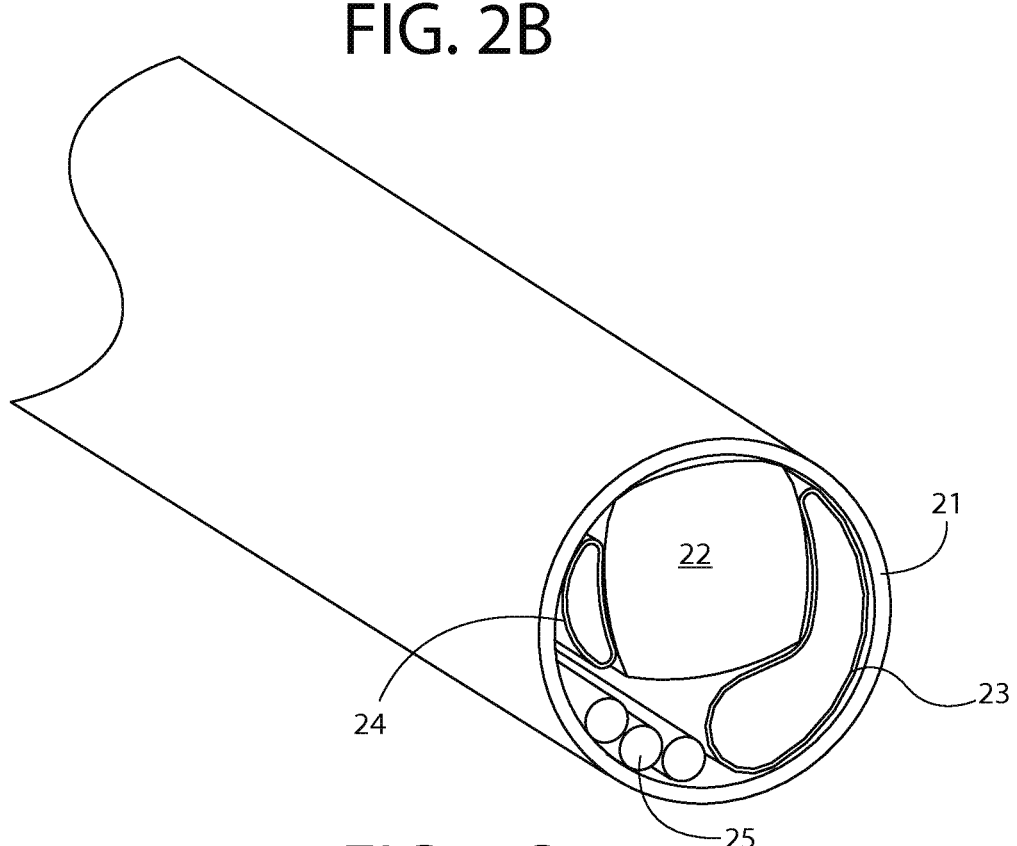
FIG. 2c is a perspective view of the expandable tip in the non-expanded configuration of an endoscope with a non-circular camera.

FIG. 2c shows the distal end of another endoscope made with a non-circular camera 22 that is radially offset from the center of the endoscope. The working channel portion 23 within the distal tip 2 and the flushing lumen 24 are adjacent the camera 22 and the elastomeric tip cover 21.

To allow the inner structures to be seen, FIG. 3 shows the endoscope of FIG. 2a without outer covers 21 and 26. The coupling sleeve 31 is a thin-wall cylindrical material that joins the elastomeric tip cover 21 and the flexible braided sheath 26. Coupling sleeve 31 depicted in FIG. 3 can be made from polyimide, stainless steel, polyurethane or other thin-wall tubing. This coupling sleeve 31 is bonded to the inside surfaces of the braided flexible sheath 26, and the elastomeric expandable tip cover 21. Joining can be by adhesive bonding, heat welding, mechanical ring-clamping or solvent bonding, or other methods for durably bonding these components.

The stylet channel 27 is a thin-wall tubing similar to that described previously for other working channels such as polyimide, PTFE, or other tubing, and which has a durable stop 33 at its distal tip, such as a plug of hard plastic such as acrylic, ABS, or other material bondable or mechanically securable to the stylet channel, which is intended to prevent the stylet from puncturing or damaging other components. The tubing also can be crimped or folded over at the end to create a stop if the tip of the stylet is rounded. This can be in addition to the hard plastic plug or instead of it.

An optional deflector ramp 34 is also shown in FIG. 3. The deflector ramp provides an angled, relatively hard surface to guide the distal tip of the tool around the proximal edge of the camera and into the distal tip expansion area of the working channel. This deflector ramp can be made of hard plastic such as acrylic or ABS, or from a thin stamped stainless steel metal piece, and may be curved to match the outside diameter of the working channel shaft. As described above in connection with FIGS. 2a and 2b, the working channel has a generally circular cross-section 28 within the shaft 3 and a variable profile section 23 within the distal tip 2. As a tool passes through the circular cross-section of the working channel shaft 28 to the variable profile working channel 23, it moves around the camera 22 and exits the distal tip of the endoscope. The ramp 34 is affixed to the endoscope. For example, the ramp can be adhered to the proximal surface of the camera 22, to the expandable work channel 23, to the sheath cover 26, or to combinations of these structures. A UV-curable epoxy or other adhesive can be used for this purpose. The ramp 34 defines an angle relative to the longitudinal axis of the endoscope that can range from about 30° to about 60°, and preferably ranges between 40° and 50°, and most preferably about 450. A ratio of the length of the ramp 34 to the overall outer diameter of the endoscope at the distal tip is less than about 1:2, preferably is less than about 1:3, and most preferably is less than about 1:5.

A coupling sleeve 35 can be used when the circular cross-section working channel shaft 28 and the expandable working channel 23 are made from different materials or different sections of tubing that are affixed together. If these are made using a single length of tubing, coupling sleeve 35 can be omitted. Unlike the outer sheath coupling sleeve 31 (which fits inside the outer cover of the expandable tip cover 21) and the flexible, braided sheath cover 26 (which allows the endoscope to maintain an even outer diameter), working channel coupling sleeve 35 fits on the outside of a joint between the circular cross-section working channel shaft 28 and the expandable working channel 23 to preserve a consistent inner diameter for tool insertion and removal. The coupling sleeve 35 can be a short piece of thin-wall polymeric tubing (e.g., a 4-5 mm of 0.0.254 mm wall thickness polyimide tubing, which is obtainable from Putnam Plastics or Vention Medical).

Figure 4:
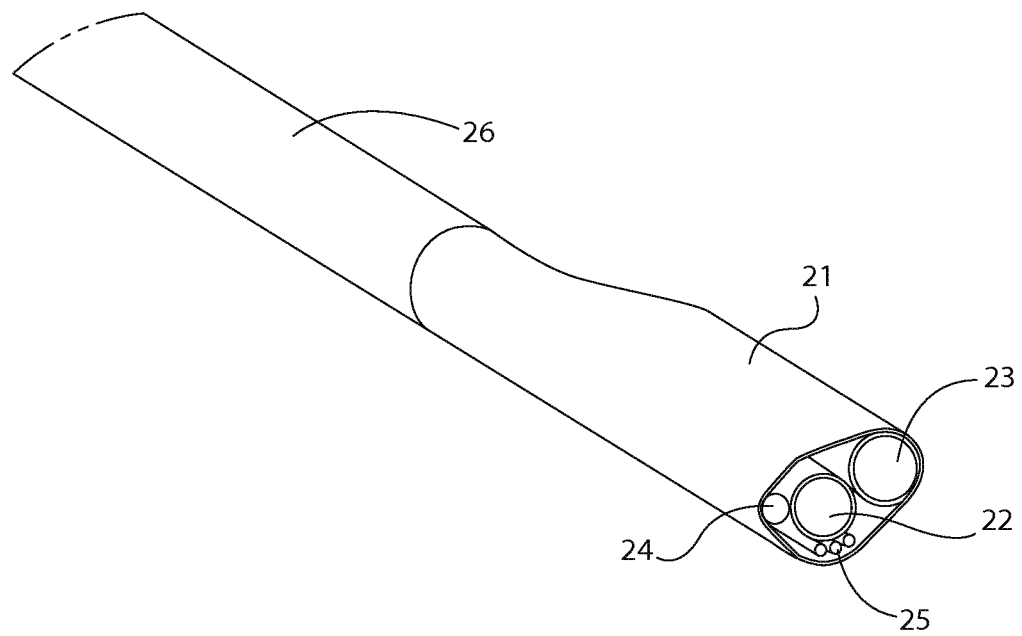
FIG. 4 is a view of the expandable tip in an expanded configuration of the endoscope of FIG. 1.

The variable profile distal tip allows the doctor to insert the endoscope through a minimal incision or puncture size (e.g., for a 12 gauge needle) while it is in a low-profile configuration. Once the endoscope is in the area to be treated, the tip section is enlarged. FIG. 4 illustrates the distal tip 2 in an enlarged-profile configuration.

Such a configuration is achieved, for example, by passing a full 1.0 mm diameter tool through the working channel tip 23, and/or flushing fluid (0.9% saline in sterile water) through the flushing channel 24 at a rate sufficient to expand the flushing channel 24 at the distal tip 2.

Figure 5:
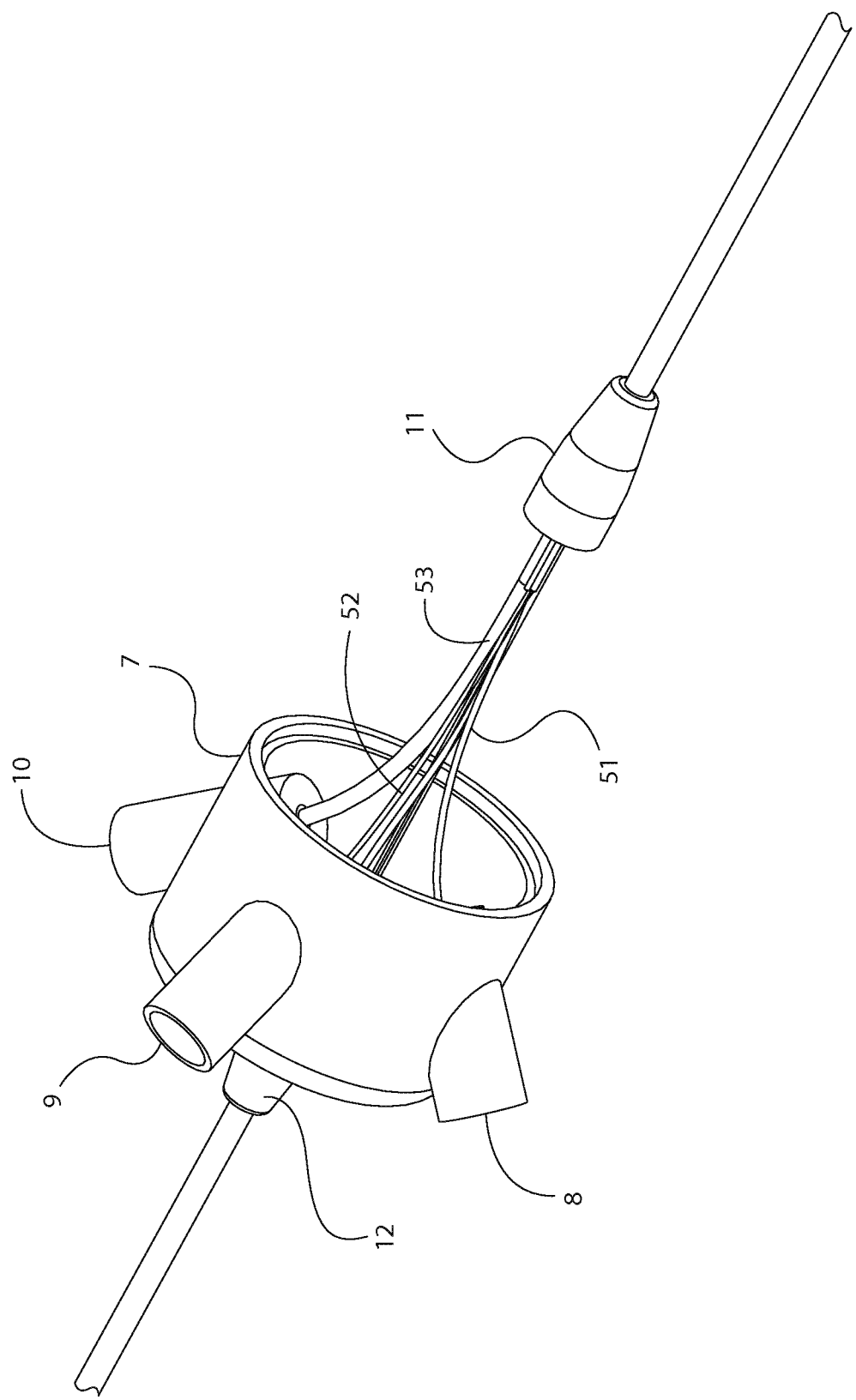
FIG. 5 is a close-up view of the coupling hub of FIG. 1 with the distal hub enclosure removed.
Figure 6:
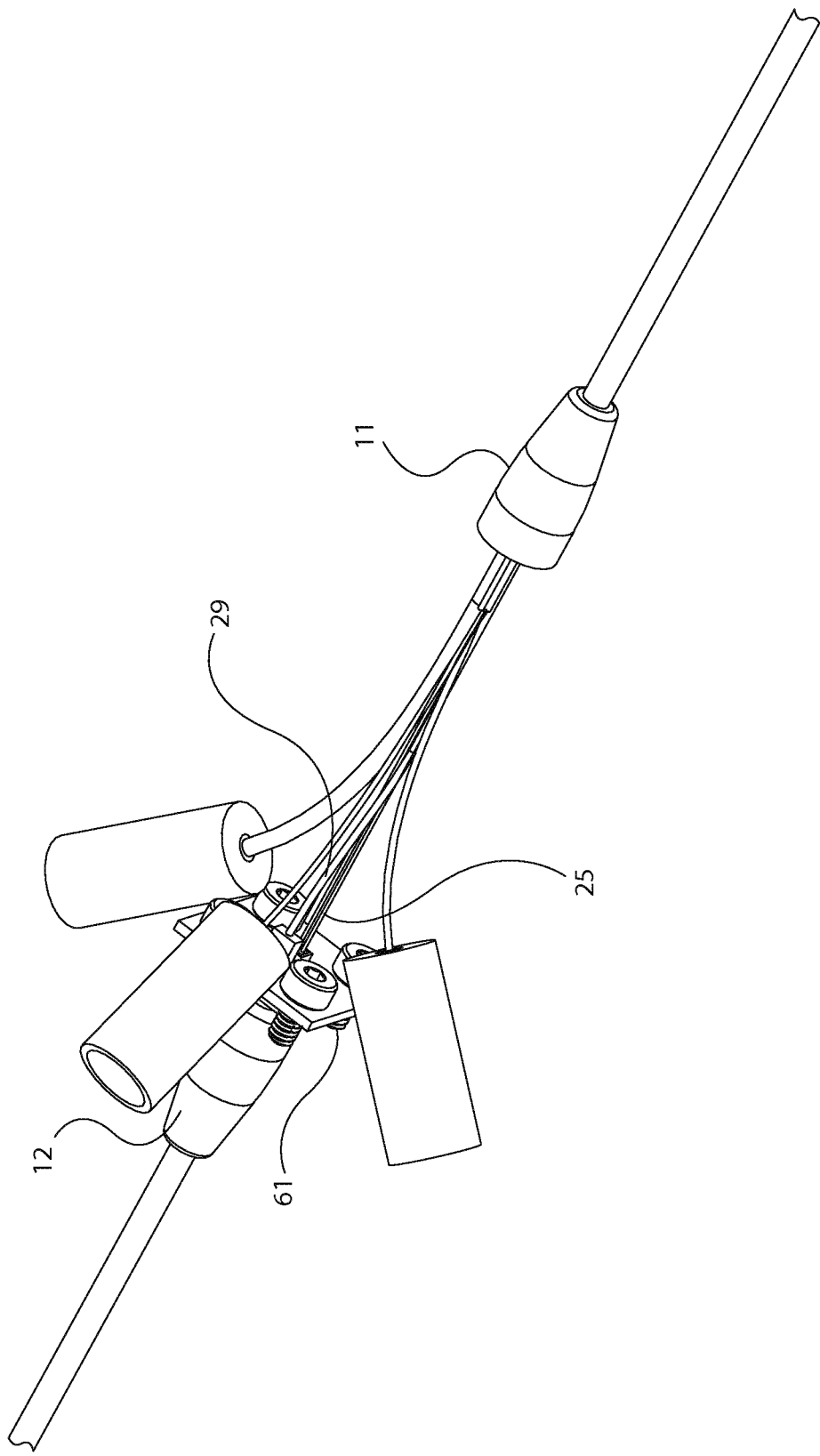
FIG. 6 is a view of components inside the coupling hub of FIG. 1 with the full enclosure removed.

FIGS. 5 and 6 show details of the coupling hub 4. In FIG. 5, the distal enclosure portion 6 is removed. The flushing channel tube 51 is attached to flushing channel connector 8. The stylet channel tube 52 is attached to the stylet channel connector 9. The working channel shaft 53 is attached to the working channel connector 10. On the proximal ends, tubes 51, 52, 53 attach to connectors, such as Luer or Luer lock connectors. Solvent bonding, adhesive bonding, or press fit can be used to make this connection.

In FIG. 6, the proximal hub enclosure 7 is removed to reveal the PCA 61, the proximal end of the camera cable 29, and the proximal end of the illumination fibers 25.

Figure 7:
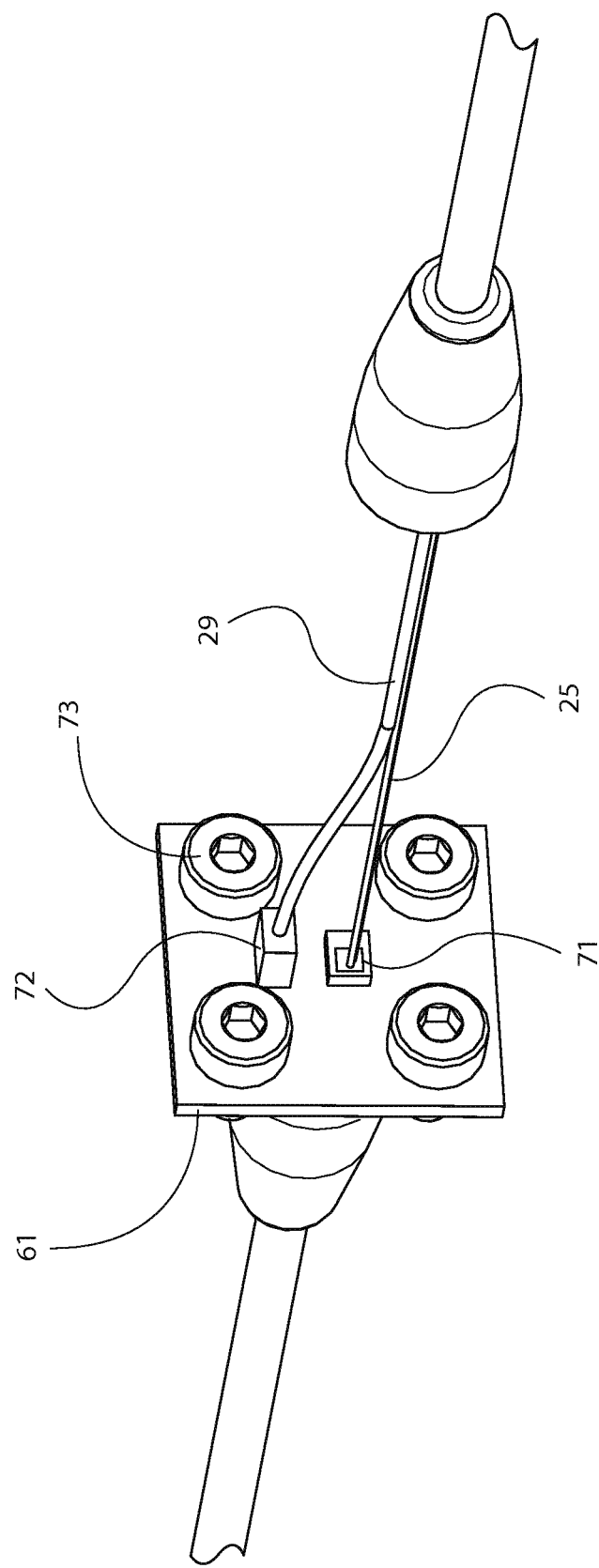
FIG. 7 is a view of the PCA (Printed Circuit Assembly) board inside the coupling hub of FIG. 1.

FIG. 7 is a close-up view of the PCA 61. Camera cable 29 connects to the PCA 61 using connector 72. LED 71 is an LED surface-mounted chip with the proximal ends of the illumination fibers 25 placed flush against the light emitting surface area of LED 71. However, non-LED illumination sources can be used (e.g., halogen incandescent, xenon light, diode lasers) so long as the particular illumination chosen can be picked up by the camera or sensor. An epoxy provides a secure attachment, although other methods can be appropriate.

Mounting screws 73 attach the PCA 61 to studs molded into the proximal hub enclosure 7. Other PCA mounting techniques can be used, including capturing the PCA 61 between the proximal hub enclosure portion 19 and the distal hub enclosure portion 6. Attachment of the two-hub enclosure portions 6, 7, the strain reliefs 11, 12 and, in turn, their attachments to the electronic cable 5, the coupling hub 4, and endoscope shaft 3 are watertight. Such watertight connections can be achieved by a number of means including flexible adhesive, solvent bonds, heat seals, rubber grommets and other seals.

The PCA 61 circuitry controls illumination intensity of the light source 71 and operates the camera 22. The PCA 61 circuits translate signals to and from an external control/display (not shown). These circuits convert signals into the patterns, voltages, timing, etc., needed by, or sent from the camera 22 and used for the illumination source 71. Such translation can include converting the signals into a Universal Serial Bus (USB) standard. Multi-layer or stacked multi-layer circuits with embedded software (e.g., firmware) and Field Programmable Logic Arrays (FPGAs) translate and communicate the signals.

If wireless communication is desired (whether RF, Infrared or another method of communication), the PCA 61 includes a wireless transceiver and a power source (e.g., battery). The battery powers the PCA 61 and the image sensor 7. The wireless transceiver interfaces with external control and display devices. For example, the PCA 61 wirelessly transmits image signals from the image sensor 7 to an external display.

Alternatively, signal translation can be accomplished externally of the endoscope. In that case, the PCA 61 functions as an interconnection and routes signals to a cable 5, which then connects to an external control/display unit (not shown).

Figure 8:
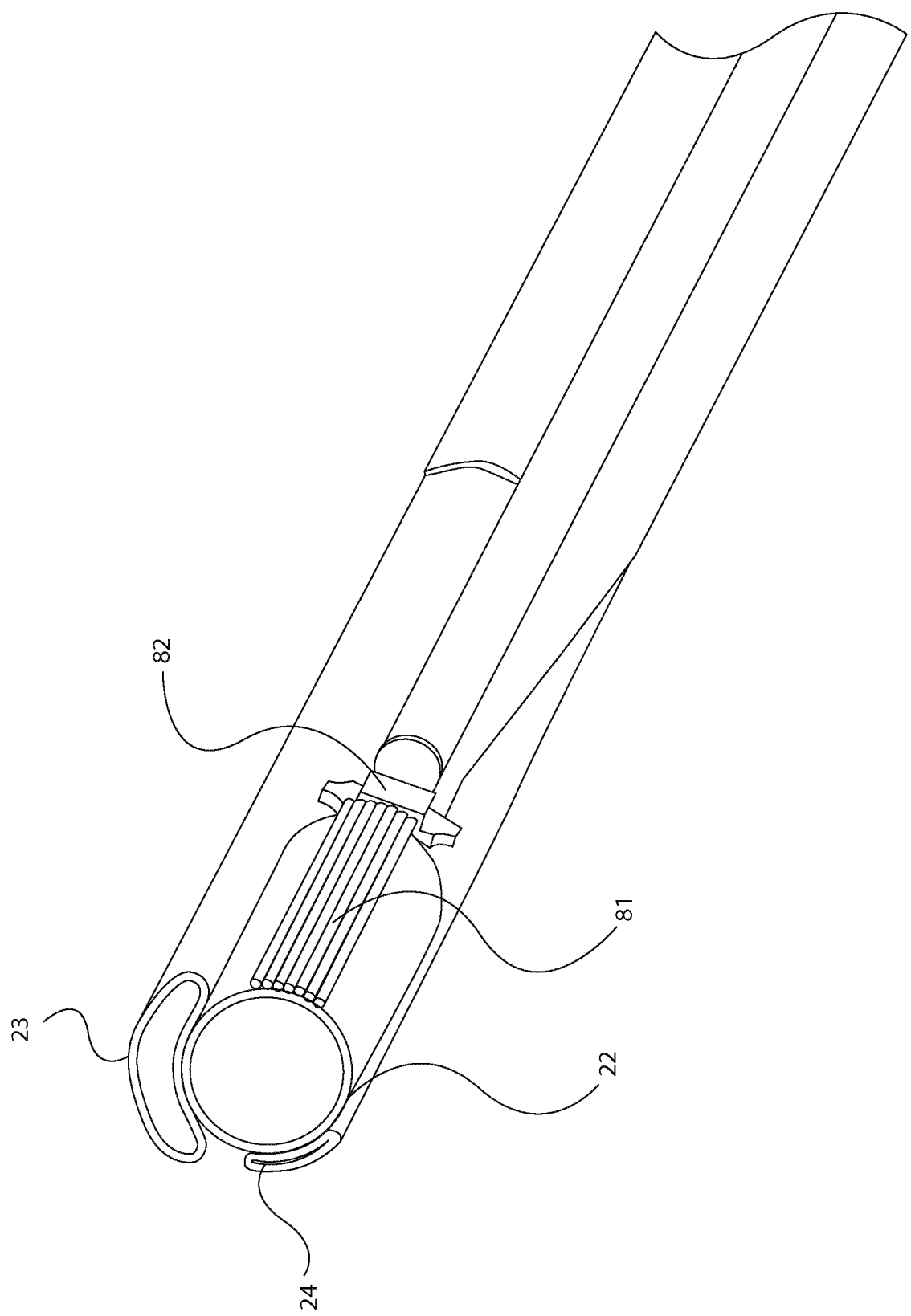
FIG. 8 is a schematic view of an endoscope illumination system.

FIG. 8 illustrates an illumination configuration for the electronic endoscope. Within the hub 4, numerous LEDs and illumination fibers or fiber bundles can be arranged to assure sufficient illumination intensity to achieve the desired field of view and depth of field. LED 82, if small enough, can be mounted adjacent to the camera 22 within the expandable tip section 2. Illumination fibers 81 are routed from the LED 82 to reach the outside of the camera 22 at the distal tip 2. Such an illumination subassembly can be rigid.

The illumination subassembly can be varied, so long as sufficient illumination intensity to achieve the desired field of view and depth of field. For example, a shaped light guide can be used to replace optical illumination fibers, as long as the Numerical Aperture and illumination field pattern of the light emitted from the light guide is compatible with the field of view of the camera 22. The LED can be mounted within the shaft section 3 or can be exterior to the endoscope, instead of within the hub enclosure 4.

The following Examples are presented to illustrate the described technology, and are not intended to limit the attached claims in any way.

Example 1

A 2 mm endoscope with expandable working channel and an LED light source in the hub similar to that shown in FIG. 1 is formed as described below. Two injection-molded ABS pieces 6, 7 (available from Dow Chemical) form the hub enclosure.

Insert cable assembly 5 with USB connector 13 (available from Molex Connector Corp.) into a strain relief tube 12 and then into a proximal opening in the proximal hub enclosure 7. The strain relief tube 12 is an injection molded component made from Shore A 60 TPE. The cable assembly 5 is electrically connected to a printed circuit assembly (PCA) 61.

PCA 61 is a small, multi-layer printed circuit board with surface mount integrated circuits to convert USB signals and communications to/from the camera into the signal levels and timing required by the camera specifications. The PCA 61 is affixed to the proximal hub enclosure 7 using four screws 73. See FIG. 7.

The proximal hub enclosure has an opening for the working channel. A working channel connector 10 provides a fluid tight seal between the proximal hub enclosure 7 and the working channel. Insert connector 10 (a commercially available LUER-LOK® lock component) into the proximal hub enclosure 7.

The sheath cover 26 is a 29.2 cm length of braided stainless steel reinforced polyimide tubing (Putnam Plastics catalog number 142-0045; 1.88 mm OD, 1.689 mm ID).

The distal strain relief tube 11 is an injection molded component made of Shore A 60 TPE. Insert this tube through an opening in hub enclosure 6. Slide the sheath cover 26 through the distal strain relief 11 for access to the interior of the hub enclosure 6. Solvent bond with cyclohexanone to affix the sheath cover 26 to distal strain relief tube 11.

The outer sheath 21/26 is formed from the polyimide and silicone tubing using a manufacturing mandrel. Slide thin-walled polyimide coupling tube 31 with an outer diameter (OD) of about 1.689 mm onto the properly sized mandrel. Then, slide an 8 mm length of silicone rubber tubing with an ID of about 1.689 mm (which will form the expandable distal tip cover 21) and the sheath/cover assembly 11, 26 onto the mandrel from opposite ends until they butt up against one another over the polyimide coupling tube 31. Bond the silicone rubber tube 21, the polyimide coupling tube 31 and the stainless steel reinforced polyimide tube 26 with cyclohexanone to create a durable joint.

The working channel is also formed using a mandrel. Slide a 29.2 cm length of polyimide tubing 28 (Vention Medical catalog number 141-0083; 0.0505 in OD×0.048 in ID) onto a mandrel of appropriate diameter. Slide an 8 mm length of USP Class 6 TPE tubing (KRATON from Kraton Polymers) onto the mandrel so it butts up against the polyimide tubing 28. Cover the resulting joint with a thin-walled polyimide coupling sleeve 35 (from Vention Medical). Join these components together with a low-viscosity ultraviolet light cure adhesive (208-CTH-F flexible, water resistant catheter bonding adhesive available from Dymax Corp.). Together the working channel assembly 23/28/35 is 30 cm long.

Slide the working channel assembly 23/28/35 into the outer sheath and previously constructed cover assembly. Connect a proximal end of the working channel assembly 23/28/35 to the working channel connector 10. Cyclohexanone solvent bonds the proximal end of the working channel to the connector 10.

Bond an acrylonitrile butadiene styrene (ABS) ramp 34 to the outside of the working channel expandable tip with cyclohexanone. Approximately the mid-point of the ramp 34 is at the rear edge of the camera 22, and the ramp provides a smooth angle for a tool to traverse into the expandable distal tip area. The ramp 34 forms an angle of 45° with respect to the longitudinal axis of the endoscope, and has a length of about 2-3 mm along that longitudinal axis.

Then, attach camera 22 to PCA 61. The camera is a micro ScoutCam™ 1.2 (Medigus, Ltd. of Omer, Israel). This camera 22 is cylindrical in shape and measures 1.2 mm in diameter by 5 mm in length, and provides an effective image resolution of about 44,880 pixels. Camera cable 29 extends from camera 22, runs within the cover assembly but along the outside of the assembled working channel, and connects to PCA 61 at the camera connector 72. See FIG. 7. PCA 61 controls camera 22 and receives images from it.

Three optical illumination fibers 25 (outer diameter of 0.25 mm, from LightHouse LEDs as catalog number 0.25 MMFIBERENDGLOW) also run within the cover assembly along the outside of the working channel assembly until they are adjacent to the camera 22. Adhere proximal ends of the illumination fibers 25 onto the light source 71, a Luxeon® C power LED (available from the Philips Lumileds Lighting Company) with UV-cured adhesive (208-CTH-F adhesive available from Dymax Corp.).

Then, seal the tip and bond the components together with Dymax adhesive.

Slide the distal hub enclosure 6 over the cover/working channel assemblies. The distal and proximal hub enclosures 6, 7 snap-fit together. Heat seal them together to obtain a liquid-tight seal.

This provides an endoscope with a 30 cm working length, a 2 mm OD, and variable profile distal tip and working channel. Such an endoscope can be used for a variety of endoscopic applications including arthroscopic joint examination and surgery for hands, shoulders, knees, etc.

Example 2

An endoscope similar to that described in Example 1 is formed with a variable profile flushing lumen 24 in addition to the variable profile working channel as illustrated in FIG. 2A. A 30 cm length of TPE tubing (Vention Medical PEBAX® tubing catalog number 115-1289; 0.0.279 mm ID, 0.1143 mm wall thickness, 0.51 mm OD, Shore A 63) forms the flushing lumen 24. The process for making the endoscope is similar to Example 1. Differences are discussed below.

Place the PEBAX® tubing adjacent to the working channel assembly 23/28/35, and push the proximal end of tubing over a barb fitting the LUER-LOK® lock connector 8. This secures the flushing lumen 24 to the proximal hub enclosure 7. Position the distal end of the flushing lumen tubing 24 adjacent the camera 22 within the expandable tip before sealing the tip.

Example 3

An endoscope similar to that described in Example 2 except the flushing lumen 24 is made from a non-expandable material. Instead of PEBAX® tubing, the flushing lumen 24 is made from polyimide tubing (Vention Medical catalog number 141-0023; 0.508 mm OD, 0.457 mm ID).

Even though the material itself is non-expandable, the flushing lumen is manufactured to provide that feature. At the distal end, heat press an 8 mm length of the polyimide tubing to form creases and a flattened end. This enables the polyimide tubing to curve around camera 22 inside the expandable outer cover 21. Place a proximal end of the polyimide tubing over the barbed connector of the commercially available connector 8 (a LUER-LOK® component) and affix it with Methyl-Ethyl-Ketone solvent.

In use, the creased and flattened distal tip of the flushing lumen 24 expands as fluid passes within the flushing lumen 24. This, in turn, expands the outer cover 21. See FIGS. 3 and 4.

Example 4

An endoscope similar to that described in Example 1 is configured for wireless communication with an external display and a control device (e.g., a PC or tablet computer). The PCA 61 has wireless transmitting and receiving components. Commonly available button-style batteries are included within the hub assembly to power PCA 61. An antenna wire is included and attached to the PCA 61. Connect a switch in series with the battery. The batteries provide sufficient power to allow the endoscope system to function for several hours.

Example 5

An endoscope similar to that described in Example 1, except the expandable working channel is a 30 cm length of non-reinforced polyimide tubing (Vention Medical catalog number 141-0083, 1.283 mm OD×1.219 mm ID). As described in Example 3 above, heat press an 8 mm length of the polyimide tubing at the distal end to form creases and a flattened end. This enables the polyimide tubing to curve around camera 22 inside the expandable outer cover 21. When a tool or other item is forced through the working channel, the creased and flattened distal tip will expand, in-turn expanding the outer cover 21, to the extent needed to allow the tool or other item to pass through.

In addition, in this example the camera 22 is an Awaiba NanEye camera (available from AWAIBA Lda). This camera 22 measures 1.1 mm×1.1 mm×1.7 mm long with a diagonal measurement of 1.41 mm, and provides an effective image resolution of about 62,500 pixels. FIG. 2c shows a cross-sectional view of this endoscope at the distal tip.

Example 6

An endoscope similar to that described in Example 1 except that it has an outer diameter of 1.7 mm.

The outer sheath 21/26 is formed from a 29.2 cm length of a braided stainless steel reinforced polyimide tubing (1.72 mm OD, 1.57 mm ID, available from Vention Medical catalog 142-0042), an 8 mm length of silicone rubber tubing with an ID of about 1.689 mm, and a thin-walled polyimide coupling tube 31 with an OD of about 1.689 mm The working channel is formed from thin-wall polyurethane tubing (Vention Medical catalog number 115-0565; 1.346 mm OD, 0.089 mm wall, 1.168 mm ID).

The camera is the NanEye camera described above in Example 5. The illumination light guides (optical fibers) are 0.125 mm OD (0.1 mm core diameter, Edmund Optics stock #57-061) and eight total fibers are used for the illumination. The four-conductor cable from the NanEye camera 22 is connected to PCA 61 for signal connection to a cable suitable for external use and possible signal processing circuits are included on PCA 61 to convert the signals to USB standards or other desired configuration. PCA 61 has memory containing calibration information for the specific NanEye camera being used.

The foregoing detailed description contains discussion of various forms of practicing the technology, and includes many specifics for the purpose of illustration. The technology is susceptible to many variations, modifications, replacements, and alternative forms based on the disclosures and suggestions described in this application without departing from the spirit and scope of the claims. Examples are used to illustrate particular embodiments; however, the claims are not intended to be limited to these examples, but rather include the full scope of the claims. Accordingly, the foregoing descriptions of the selected embodiments and following examples are set forth without any loss of generality to, and without imposing limitations upon, the described technology.

Further, in the foregoing detailed description of the selected embodiments, reference is made to the accompanying drawings that form a part hereof, and in which are shown by way of illustration specific embodiments in which the described technology can be practiced. Other embodiments can be utilized and structural changes can be made without departing from the scope of the described technology. For instance, general principles and features illustrated or described as part of one embodiment can be used in another embodiment to yield a still further embodiment without departing from the spirit and scope of the described technology. Accordingly, the scope of the claims is not limited by the above description. All changes, which come within the meaning and range of equivalency of the claims, are to be embraced within their scope.

What we claim is:

1. An endoscope comprising:
a hub;
a shaft extending from the hub, the shaft having an outer dimension;
a distal tip extending from a distal portion of the shaft;
an image sensor within the distal tip, the image sensor having a field of view external to the endoscope;
an illuminating element configured to emit light within the field of view of the image sensor;
a first working channel tube disposed within the shaft and extending continuously from a proximal end at the hub to a distal end within the distal tip, the first working channel tube comprising a first portion within the distal tip, wherein the first portion of the first working channel tube is configured to expand to an enlarged configuration to accommodate passage of a first object,
wherein the distal tip has a dimension greater than the outer dimension, when the first portion of the first working channel tube has the enlarged configuration, and
wherein the first working channel tube is configured to accommodate passage of the first object through a proximal portion of the shaft while maintaining the outer dimension of the shaft; and
a second working channel tube disposed within the shaft generally parallel with the first working channel tube and extending continuously from a proximal end at the hub to a distal end within the distal tip, the second working channel tube comprising a second portion within the distal tip, wherein the second portion of the second working channel tube is adapted to expand to an enlarged configuration to accommodate passage of a second object,
wherein the distal tip has a dimension greater than the outer dimension when the second portion of the second working channel tube has the enlarged configuration, and
wherein the second working channel tube is configured to accommodate passage of the second object through the proximal portion of the shaft while maintaining the outer dimension of the shaft; and
wherein the image sensor is located between the first working channel tube and the second working channel tube and the first working channel tube and the second working channel tube are separated by the image sensor, and expansion of the first portion of the first working channel tube to the enlarged configuration radially expands the distal tip in a first direction, expansion of the second portion of the second working channel tube to the enlarged configuration radially expands the distal tip in a second direction, generally opposed to the first direction, the distal tip having a greater dimension when either or both of the first and second working channel tubes expand to their enlarged configuration such that expansion of the first and second portions cause corresponding expansion of the distal tip.

2. The endoscope of claim 1, wherein the first working channel tube and the second working channel tube are angularly separated around a circumference of the distal tip by about 120°.

3. The endoscope of claim 1, wherein the first working channel tube and the illuminating element are angularly separated around a circumference of the distal tip by about 120°.

4. The endoscope of claim 1, wherein the image sensor comprises a circular cross-sectional shape.

5. The endoscope of claim 1, wherein the image sensor comprises a noncircular cross-sectional shape.

6. The endoscope of claim 1, wherein the illuminating element comprises an illumination fiber.

7. The endoscope of claim 1, wherein the illuminating element is located at least partially within the distal tip.

8. The endoscope of claim 1, further comprising an illumination source in communication with the illuminating element, wherein the illumination source is located in the hub.

9. The endoscope of claim 1, further comprising an illumination source in communication with the illuminating element, wherein the illumination source is located in the distal tip.

10. The endoscope of claim 1, wherein the first object comprises a tool.

11. The endoscope of claim 1, wherein the first object comprises a fluid.

12. The endoscope of claim 1, wherein the first object comprises a first tool and the second object comprises a second tool.

13. The endoscope of claim 1, wherein an outer diameter of the distal tip has a reduced cross-sectional area with an outer diameter of between about 1.5 mm and 5 mm.

14. The endoscope of claim 1, wherein the distal tip is further configured for positioning the distal tip at a specified location within a patient.

15. The endoscope of claim 8, wherein the illumination source is selected from the group consisting of: an LED illumination source, a halogen illumination source, an incandescent illumination source, a xenon light illumination source, and a diode laser illumination source.

16. The endoscope of claim 9, wherein the illumination source is selected from the group consisting of: an LED illumination source, a halogen illumination source, an incandescent illumination source, a xenon light illumination source, and a diode laser illumination source.

17. The endoscope of claim 10, wherein the tool is selected from the group consisting of: an ablation device, a cannula, a dissector, an electrode, a forceps, a grasper, a knot pusher, a laser fiber, a needle holder, a suction device, an irrigation instrument, and a trocar.

18. An endoscope comprising:
a hub;
a shaft extending from the hub, the shaft having a shaft width;
a distal tip extending from the shaft;
an image sensor located at least partially within the distal tip, the image sensor having a field of view external to the endoscope;
an illuminating element configured to emit light within the field of view of the image sensor;
a first channel tube extending continuously from the hub to the distal tip, the first channel tube having a proximal portion located at least partially within the shaft and a distal portion located at least partially within the distal tip, wherein the proximal portion of the first channel tube is configured to accommodate passage of a first object within the shaft width,
wherein the distal portion of the first channel tube is configured to expand from a first width to a second width to accommodate passage of the first object through the first channel tube, wherein the distal tip has a width greater than the shaft width when the first channel tube is expanded to the second width; and
a second channel tube extending continuously from the hub to the distal tip, the second channel tube having a proximal portion located at least partially within the shaft and a distal portion located at least partially within the distal tip, wherein the proximal portion of the second channel tube is configured to accommodate passage of a second object within the shaft width,
wherein the distal portion of the second channel tube is configured to expand from a third width to a fourth width to accommodate passage of the second object through the second channel tube, wherein the width of the distal tip is greater than the shaft width when the second channel tube is expanded to the fourth width;
wherein expansion of the first channel tube and the second channel tube cause corresponding expansion of the distal tip.

19. The endoscope of claim 18, wherein the distal portion of the first channel tube is configured to expand from a lunate cross-sectional shape having the first width to a rounded cross-sectional shape having the second width.

20. The endoscope of claim 19, wherein the distal portion of the second channel tube is configured to expand from a lunate cross-sectional shape having the third width to a rounded cross-sectional shape having the fourth width.

* * * * *